US009517213B2

(12) United States Patent
Daeef

(10) Patent No.: US 9,517,213 B2
(45) Date of Patent: Dec. 13, 2016

(54) KIT CONTAINING PATCHES AND COMPOSITION FOR INSECT BITE TREATMENT

(71) Applicant: Umm Al-Qura University, Makkah (SA)

(72) Inventor: Salha F. H. Daeef, Makkah (SA)

(73) Assignee: Umm Al Qura University, Makkah (SA)

( * ) Notice: Subject to any disclaimer, the term of this patent is extended or adjusted under 35 U.S.C. 154(b) by 0 days.

(21) Appl. No.: 14/643,020

(22) Filed: Mar. 10, 2015

(65) Prior Publication Data

US 2016/0263049 A1 Sep. 15, 2016

(51) Int. Cl.
*A61K 9/70* (2006.01)
*A61K 36/88* (2006.01)
*A61K 36/23* (2006.01)
*A61K 45/06* (2006.01)

(52) U.S. Cl.
CPC ............ *A61K 9/7084* (2013.01); *A61K 36/23* (2013.01); *A61K 36/88* (2013.01); *A61K 45/06* (2013.01)

(58) Field of Classification Search
CPC ..................................................... A61K 9/7084
See application file for complete search history.

(56) References Cited

U.S. PATENT DOCUMENTS

| 2009/0258044 A1* | 10/2009 | Mosher | A01N 43/40 424/406 |
| 2009/0306025 A1* | 12/2009 | Lane | A61K 31/18 514/161 |
| 2014/0163447 A1* | 6/2014 | Wieland | A61L 15/28 602/47 |

FOREIGN PATENT DOCUMENTS

WO    WO 2013007732 A1 *   1/2013   ............. A61L 15/28

* cited by examiner

*Primary Examiner* — Benjamin Packard
(74) *Attorney, Agent, or Firm* — Dennis H. Lambert

(57) ABSTRACT

A kit for treating insect bites includes a plurality of patches of different size and shape, and a container of a composition containing extracts of garlic and parsley. The patches have a pad bordered by a margin coated with a pressure sensitive adhesive. The extracts of parsley include apiol and myristicin, and the extracts of garlic include allicin. In use, the composition is deposited onto the pad and the patch is placed over an affected area and adhered to the skin with the pressure sensitive adhesive.

13 Claims, 4 Drawing Sheets

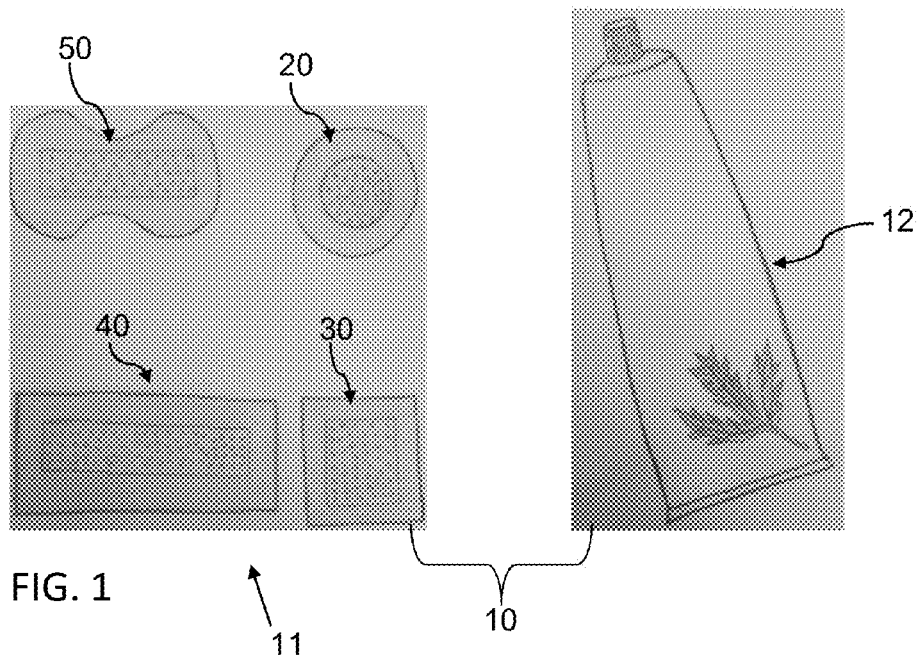
FIG. 1
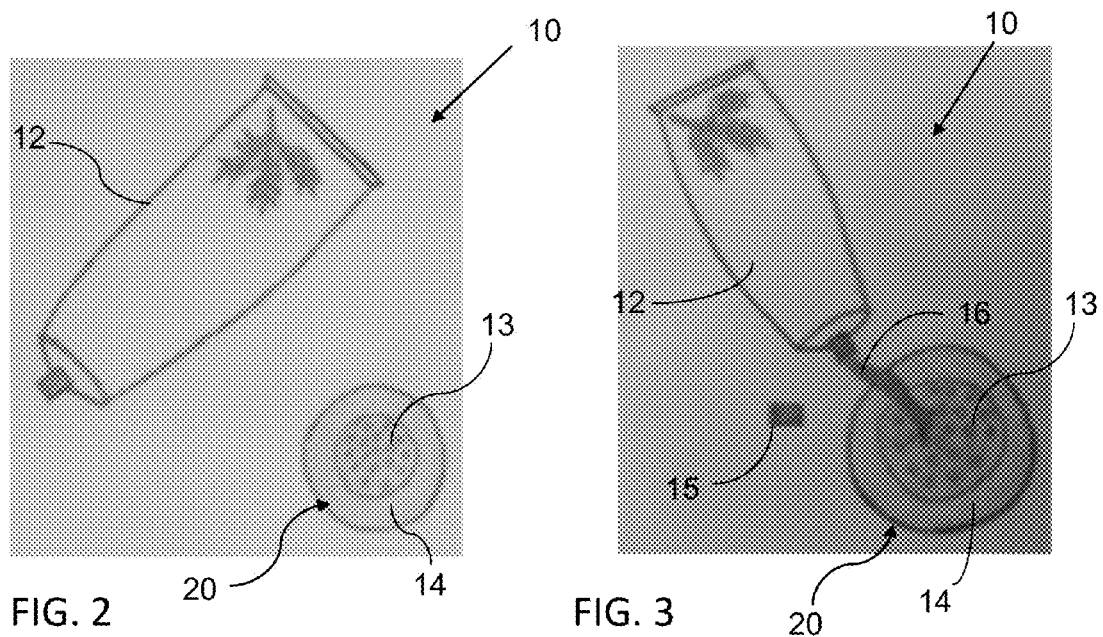
FIG. 2
FIG. 3

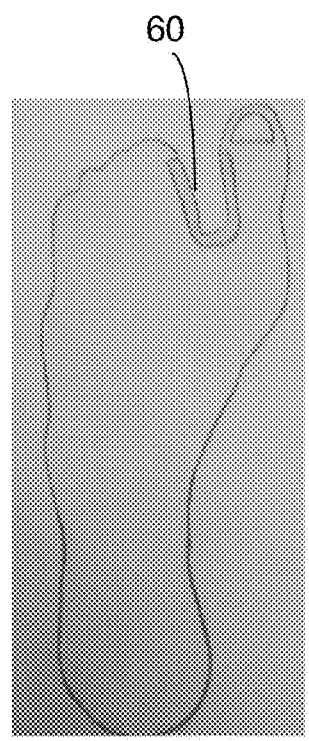 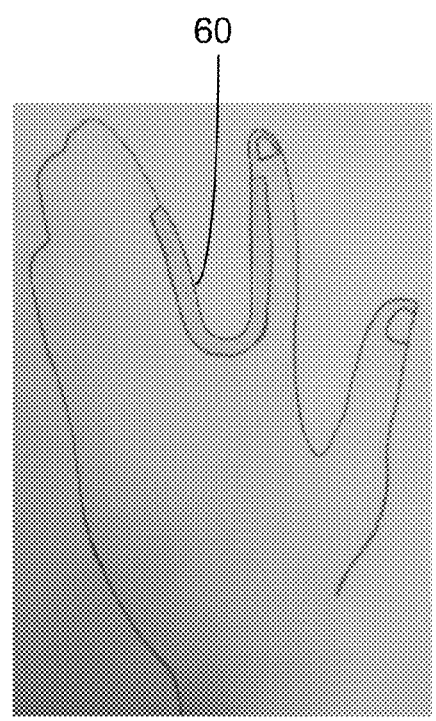
FIG. 11                    FIG. 12

KIT CONTAINING PATCHES AND COMPOSITION FOR INSECT BITE TREATMENT

FIELD OF THE INVENTION

This invention relates generally to the treatment of insect bites, and more particularly to a kit that contains patches for adhesive attachment to the skin and a composition that is applied to the patch for treatment of the bites when the patch is applied over the affected area.

BACKGROUND ART

Insect bites and stings generally cause itching, swelling and pain in the affected area. Numerous treatments are known in the art for treating and relieving these symptoms, including the use of antihistamine administered orally or in severe cases by injection, and/or by the topical applications of various compositions of salves, ointments and lotions.

Transdermal patches for treating insect bites are also known in the art as exemplified in U.S. Pat. No. 8,475,836 and Canadian patent 2,147,595. U.S. Pat. No. 8,475,836 discloses a topical patch that contains an adhesive gel composition that includes a cooling agent such as menthol or an acrylic amide for example, a water-soluble polymer gel, water, and a water holding agent. Canadian patent 2,147,595 discloses an insect repellant patch having an absorbent pad impregnated with a liquid insect repellant containing citronella oil, wherein the pad has a coating of pressure-sensitive adhesive.

Published international application WO 2008/133,982 discloses a transdermal patch having a cotton backing that can contain a variety of medicaments, including garlic, for treating a variety of ailments. Garlic is described in the patent as an anti-viral agent. The patent mentions that the patch can be used for treating insect bites.

Parsley is historically known to be useful in treating insect bites (*Parsley Uses, Benefits & Side Effects*, Drugs.com Herbal Database, Feb. 22, 2014) but the manner in which it has been used is not known to applicant and the noted reference does not explain.

Applicant is not aware of any prior system for treating insect bites that comprises a kit containing patches and a separate container of a medicament that is applied to a patch by the user at the time the patch is to be adhesively secured over the affected site. Applicant also is not aware of a prior system for treating insect bites with a composition of parsley and garlic extracts.

It would be desirable to have a system for treating insect bites that comprises a kit containing patches and a separate container of a medicament that is applied to a patch by the user at the time the patch is to be adhesively secured over the affected site, and wherein the medicament comprises a composition of parsley and garlic extracts.

SUMMARY OF THE INVENTION

The present invention is a kit for treating insect bites, wherein the kit comprises patches and a separate container of a medicament that is applied to a patch by the user at the time the patch is to be adhesively secured over the affected site, wherein the medicament comprises a composition containing parsley and garlic extracts.

More specifically, the system of the invention comprises a kit having a plurality of patches of different size and shape for application to different parts of the body, wherein the medicament is applied by the user to a cotton pad on the patch and a portion of the patch bordering the pad has a pressure sensitive adhesive to secure the patch over the affected site.

The medicament in the system of the invention has anti-bacterial properties and is effective in reducing swelling and discomfort associated with the insect bite. In preparing a composition according to the invention, 10 grams of mashed garlic, 2 grams of alcohol, and 90 grams of water are mixed with 100 grams of ground parsley.

BRIEF DESCRIPTION OF THE DRAWINGS:

The foregoing, as well as other objects and advantages of the invention, will become apparent from the following detailed description when taken in conjunction with the accompanying drawings, wherein like reference characters designate like parts throughout the several views, and wherein:

FIG. 1 is an exploded view of a kit comprising an assortment of patches and a tube of medicament according to the invention.

FIG. 2 is a view of one of the patches and a tube of medicament from the kit.

FIG. 3 is a view similar to FIG. 2, showing the tube of medicament opened and the medicament being applied to the patch.

FIGS. 9-12 are views showing use of the different patches on different parts of the body.

DETAILED DESCRIPTION OF THE PREFERRED EMBODIMENTS

Figure 4:
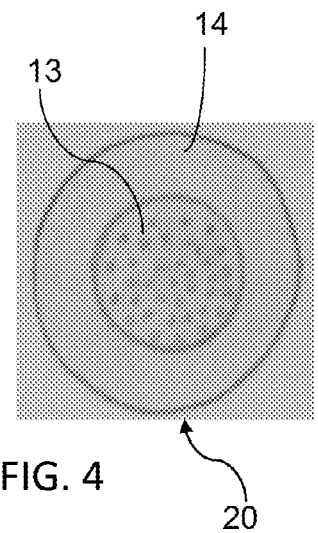
FIGS. 4-8 are plan views of different size and shape patches for use in the invention.
Figure 5:
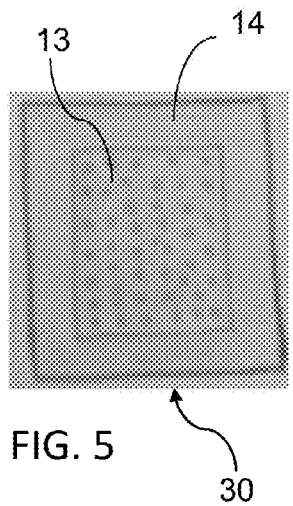
Figure 6:
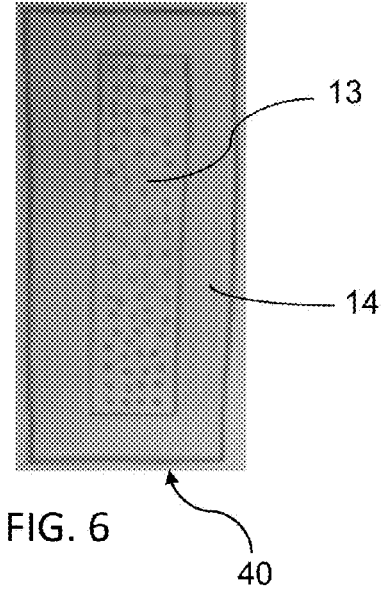
Figure 7:
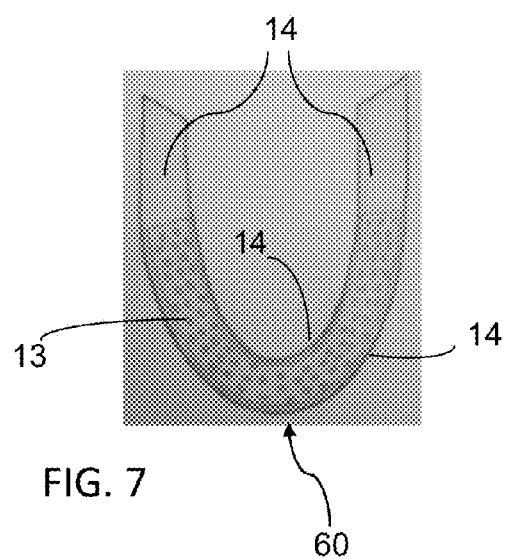
Figure 8:
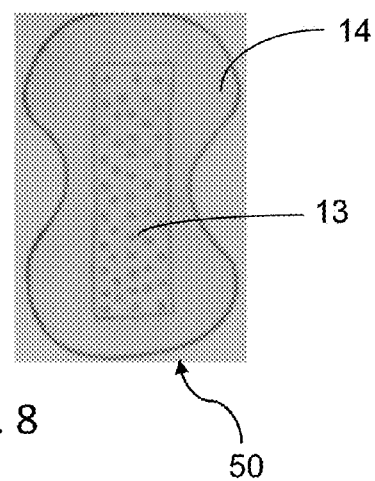
Figure 9:
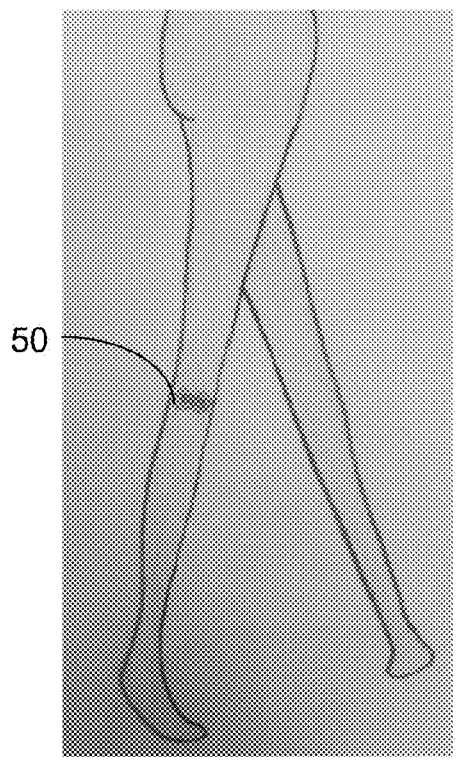
Figure 10:
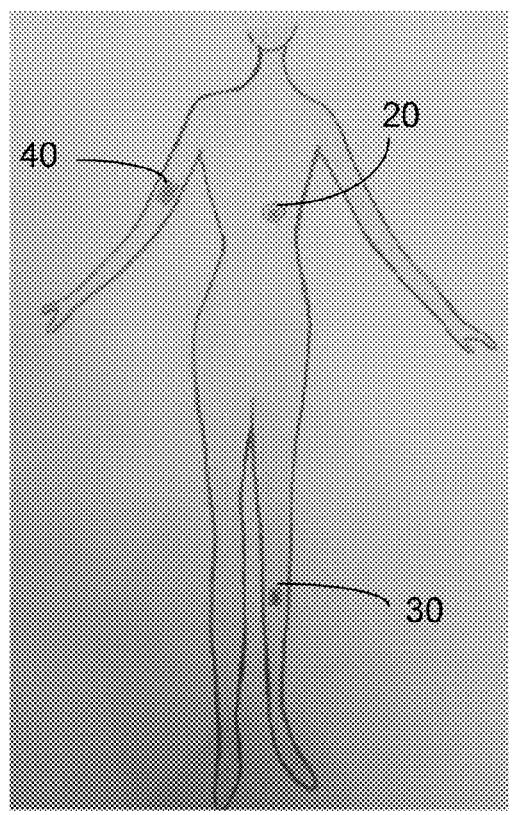

A kit for treating insect bites is indicated generally at 10 in FIGS. 1-3. The kit comprises an assortment 11 of patches and a container 12 of medicament. As shown in the drawings the container 12 comprises a squeezable tube for dispensing a cream or paste-like medicament, but the medicament could be dispensed from another type of applicator, such as, for example, as a spray or droplets, etc., as suitable for the intended purpose. The patches include a circular patch 20, a square patch 30, a rectangular patch 40, a generally peanut shell shaped patch 50, and as shown in FIG. 7, a horseshoe shaped patch 60. The patches shown in FIGS. 1-8 are examples of the variety of patches that could be included in the kit, but the invention is not limited to the examples shown and other shapes and sizes could be provided in the kit. The container preferably comprises a squeezable tube, but other types of container could be used.

FIGS. 2 and 3 show the tube 12 and one of the patches 20. The patch 20 is circular and has a cotton pad 13 in its center, with an annular border coated with a pressure sensitive adhesive 14. In use, the cap 14 is removed from the tube and a quantity of the medicament 16 is squeezed onto the pad. The patch is then placed over the affected area and adhered to the skin.

As described in more detail hereinafter, the medicament comprises a composition that includes apiol and myristicin extracted from parsley, and allicin extracted from garlic, as the main active ingredients. Parsley is rich in vitamins A, B, C and K and is a natural healer. Allicin, a key ingredient of garlic, and helps heal cuts and wounds. The composition has antibacterial properties, thus reducing the risk of bacterial infection at the site of an insect bite. It also speeds healing and reduces swelling, itching and pain at the site of the bite.

In preparing a composition according to the invention, mashed garlic, alcohol and water are mixed in the following proportions: 10 grams mashed garlic; 2 grams alcohol; and 90 grams water. This is mixed with 100 grams of ground parsley. Volatile oils in the mixture include myristicin (apiol), retinol (vitamin A), ascorbic acid (vitamin C), phyllo quinone (vitamin K), folic acid (vitamin B), and allyl propyl (allicin). One gram of parsley contains 40.4 micrograms of vitamin A, 5.48 micrograms of vitamin K, 1.65 milligrams of vitamin C, 0.4 milligrams of vitamin B, 6 grams of allicin, 0.2 grams of apiol, and 0.2 grams of myristicin.

Common to all of the patches 20, 30, 40, 50 and 60, regardless of their size and shape, is a pad 13 bordered by a margin coated with a pressure sensitive adhesive 14. The pad preferably is made of cotton, but other suitable materials could be used. Patches of different size and shape can be selected for application to different parts of the body, as depicted in FIGS. 9-15.

While particular embodiments of the invention have been illustrated and described in detail herein, it should be understood that various changes and modifications may be made in the invention without departing from the spirit and intent of the invention as defined by the appended claims.

What is claimed is:

1. A kit for treating insect bites, comprising:
   a plurality of patches of different size and shape, said patches having a pad bordered by a margin coated with a pressure sensitive adhesive; and
   a container of medicament comprising a composition containing extracts of garlic and parsley, said medicament being deposited onto said pad and the patch being placed over an affected area and adhered to the skin when the kit is used to treat an insect bite, wherein said composition comprises a mixture of 10 grams of mashed garlic, 2 grams of alcohol, 90 grams of water, 100 grams of ground parsley, and volatile oils myristicin, retinol, ascorbic acid, phyllo quinone, folic acid, and allyl propyl.

2. A kit as claimed in claim 1, wherein:
   said extracts of garlic comprise allicin; and
   said extracts of parsley comprise apiol and myristicin.

3. A system as claimed in claim 2, wherein:
   said composition includes vitamin A, vitamin B, vitamin C and vitamin K.

4. A composition for topical treatment of insect bites, comprising a mixture of:
   10 grams of mashed garlic, 2 grams of alcohol, 90 grams of water, 100 grams of ground parsley, and volatile oils myristicin, retinol, ascorbic acid, phyllo quinone, folic acid, and allyl propyl.

5. The composition as claimed in claim 4, wherein:
   There are 40.4 micrograms of vitamin A, 5.48 micrograms of vitamin K, 1.65 milligrams of vitamin C, 0.4 milligrams of vitamin B, 6 grams of allicin, 0.2 grams of apiol, and 0.2 grams of myristicin.

6. The kit as claimed in claim 2, wherein:
   said pad is made of cotton.

7. The kit as claimed in claim 6, wherein:
   said patches include a patch and associated pad having generally a horseshoe shape, said horseshoe shaped patch being adapted to be applied between fingers and toes.

8. The kit as claimed in claim 6, wherein:
   said patches include a patch and associated pad having a circular shape.

9. The kit as claimed in claim 6, wherein:
   said patches include a patch and associated pad having a square shape.

10. The kit as claimed in claim 6, wherein:
    said patches include a patch and associated pad having an elongate rectangular shape.

11. The kit as claimed in claim 6, wherein:
    said patches include a patch having a butterfly shape with a rectangular pad centered on it.

12. The kit as claimed in claim 6, wherein:
    said composition includes vitamin A, vitamin B, vitamin C and vitamin K.

13. The kit as claimed in claim 3, wherein:
    there are 40.4 micrograms of vitamin A, 5.48 micrograms of vitamin K, 1.65 milligrams of vitamin C, 0.4 milligrams of vitamin B, 6 grams of allicin, 0.2 grams of apiol, and 0.2 grams of myristicin.

* * * * *